(12) United States Patent
Klyachko et al.

(10) Patent No.: US 6,635,869 B2
(45) Date of Patent: Oct. 21, 2003

(54) STEP FUNCTION DETERMINATION OF AUGER PEAK INTENSITY

(75) Inventors: Dimitri Klyachko, Cupertino, CA (US); Sergey Borodyansky, Cupertino, CA (US); Leonid Vasilyev, Sunnyvale, CA (US)

(73) Assignee: FEI Company, Hillsboro, OR (US)

( * ) Notice: Subject to any disclaimer, the term of this patent is extended or adjusted under 35 U.S.C. 154(b) by 325 days.

(21) Appl. No.: 09/792,990

(22) Filed: Feb. 26, 2001

(65) Prior Publication Data

US 2002/0145111 A1 Oct. 10, 2002

(51) Int. Cl.[7] .............................. H01J 37/05; H01J 49/48
(52) U.S. Cl. ...................... 250/305; 250/306; 250/307; 250/310
(58) Field of Search ............................... 250/305, 306, 250/307, 310, 397

(56) References Cited

U.S. PATENT DOCUMENTS 4,034,220 A * 7/1977 le Gressus et al. ......... 250/310
5,231,287 A * 7/1993 Sekine et al. ............... 250/305
5,315,113 A * 5/1994 Larson et al. ............... 250/305
5,464,978 A * 11/1995 Kudo et al. ................. 250/305
6,399,944 B1 * 6/2002 Vasilyev et al. ............ 250/310

* cited by examiner

Primary Examiner—Nikita Wells
(74) Attorney, Agent, or Firm—Michael O. Scheinberg

(57) ABSTRACT

An electron analyzer and its method of operation useful for determining the intensity of a peak in the electron spectrum. The invention is particularly useful for determining the intensity of an Auger peak of a given element in the sample being probed and associating the intensity with a concentration of that element in the sample. The electron spectrum is measured above and below the anticipated peak. The data near the peak are not used. The remaining data above the peak and below the peak are fit to respective equations linearly dependent upon the measurement energy. The difference of the two equations at the value of the peak energy is associated with the peak intensity and the elemental concentration. The invention can be applied to measuring nitrogen concentration in a thin protective film of amorphous carbon or diamond.

14 Claims, 3 Drawing Sheets

STEP FUNCTION DETERMINATION OF AUGER PEAK INTENSITY

FIELD OF THE INVENTION

The invention relates generally to electron spectroscopy. In particular, the invention relates to a method of determining the intensity of an electron spectroscopic peak.

BACKGROUND ART

Many technologically advanced devices rely upon composite structures having a very thin, substantially planar film covering a substrate of another material. An example of such a device is a magnetic recording or read head which has an active surface layer of a ferromagnetic material. High-performance ferromagnetic materials based on, for example, heavier elements such as cobalt, are often brittle and subject to oxidation so that it is common practice to cover the ferromagnetic layer with a very thin protective layer, often of a carbon-based material such as diamond. However, the performance and durability of such devices depend on the manufacturing process to produce a uniform covering layer of diamond with a limited fraction of impurities. Excessive impurities would degrade the ability of the covering layer to protect the underlying ferromagnetic film.

Auger electron spectroscopy, to be described below, is commonly used for determining the composition of surface layers, often of thickness of 6 nm and less. Auger spectroscopy is a type of electron spectroscopy relying upon complex atomic interactions. Briggs et al. have edited a complete reference of Auger and other electron spectroscopy in *Practical Surface Analysis*, vol. 1, *Auger and X-ray Photoelectron Spectroscopy*, $2^{nd}$ ed., (Wiley, 1990). In the typical practice of Auger spectroscopy, the solid is probed with an electron beam in the low keV range of energies and produces a secondary electron through an Auger transition process having a well defined Auger energy $E_{AUGER}$. In Auger spectroscopy, the probing radiation ejects an inner-shell electron from an atom. Then in the Auger transition, a first outer-shell electron falls into the inner-shell vacancy and a second outer-shell electron is ejected carrying the difference in energy. The spectrometer analyzes the energy of the ejected electron as the Auger energy $E_{AUGER}$. The Auger energy $E_{AUGER}$ is for the most part unique for each atom, primarily dependent upon the atomic number Z. Thus, the measured electron energy can be used to determine the composition of the material, at least near its surface. These energies are generally in the range of a few hundred eV to a few keV for the typical practice of Auger electron spectroscopy. Usually to enhance the Auger signal, the primary energy $E_p$ is made twice or more the Auger energy $E_{AUGER}$. Auger electron spectroscopy allows the very quick and highly accurate measurement of film thicknesses up to about 30 nm. Other types of electron spectroscopy are possible with similar equipment, and the technology is close to electron microscopy.

A generic electron spectrometer is schematically illustrated in FIG. 1. Other geometrical relationships may be used. An electron gun 10 emits a primary radiation beam 12 of electrons of energy $E_p$ towards a sample 14 under test, which is supported on a holder 16. An electron energy analyzer 18 receives a beam 20 of secondary electrons emitted from the sample 14 and characterized by energy $E_s$. The low electron energies require that the entire analyzer be operated at very high vacuum levels. The secondary beam 20 tends to be spatially very broad. The electron energy analyzer 18 typically has a spatially fixed entrance slit 22 to fix the angle between the analyzer 18 and the sample 14, and it internally analyzes the secondary energy $E_s$ by means of a electrostatic retarder or a magnetic analyzer or other means. Although in some automated applications, the electron analyzer 18 outputs a small number of experimentally determined parameters, the typical analyzer at some level outputs an energy spectrum from which the energy location of one or more peaks is extracted. Modern spectrometers are typically operated under software control by a computer 24, which stores spectrometer data as it is being generated in a memory 26. This design allows the computer 24 to intensively analyze the the entire spectrum after it has been accumulated 26. Such electron spectrometers are well known, very often as Auger or ESCA spectrometers, and are commercially available from several sources, including Physical Electronics (PHI), a division of Perkin-Elmer of Eden Prairie, Minn., Vacuum Generators of the United Kingdom, and Omicron of Delaware.

A major experimental effect in electron spectroscopy is background noise introduced by elastic and inelastic scattering of the primary electrons as they enter the material being tested and scattering of secondary electrons as they pass through the material between their points of interaction with the constituent atoms of the material and the surface of the material. All electrons experience both elastic and inelastic collisions. Inelastically scattered electrons have a wide distribution of energies beginning at the energy $E_p$ of the probing beam and extending downwardly. The elastically scattered spectrum is typically larger because of the small Auger cross sections.

Primary electrons used for Auger spectroscopy typically have energies of a few keV while the Auger transitions are typically below 1 keV. A 1 keV electron has a mean free path in a solid of about 3 nm; a 3 keV electron, 15 nm. Furthermore, secondary Auger electrons are subject to the same type of inelastic scattering. Many technical articles have attempted to explain and quantify the effects of inelastic scattering in order to extract the Auger spectrum. Elastic scattering depends upon the average atomic number Z of the material and is stronger in materials with higher Z.

Auger spectroscopy may be used for two different purposes in determining the purity of a layer. The energy of the Auger peaks can be easily identified with the atomic number of a constituent of the film. Thereby, the atomic composition of the impurity can be relatively easily identified, that is, whether it is nitrogen or iron, for example in a carbon film. The more demanding task is to use Auger spectroscopy for determining a concentration of the impurity, a capability enabled by the fact that the size of the Auger peak increases with the concentration of the particular impurity. However, Auger spectroscopy is poorly suited for compositional measurements in otherwise poorly characterized samples, particularly those of complex composition, because the Auger peak is almost always only a small fraction of the background signal mostly originating from the elastic scattering of the primary electrons.

The conventional method for extracting an Auger peak and its magnitude takes advantage of the fact that the background signal tends to change slowly with the electron energy, as schematically graphed in FIG. 2, while the Auger peaks 30 represent narrow features located on an energy that is unique for each chemical element. Therefore, one of various techniques is used to determine the derivative of the electron intensity spectrum N(E) with respect to energy, that is dN(E)/dE, as schematically graphed in FIG. 3 for the same data. The slowly changing background nearly disappears in the derivative data facilitating the measurement of the signal intensity. In the past, analog methods were used for synchro-detection of the intensity with respect to a dither signal applied to the energy. On the other hand, in modem spectrometers, a complete energy spectrum N(E) is measured and stored in computer memory, and numerical methods are used to produce the differentiated spectrum. Conventionally, the intensity of the differentiated spectrum is measured as the difference amplitude 38 of the signal between its maximum value 34 and minimum value 36. However, this method lacks precision as it depends on the shape of the peak, which in turn depends on the spectral resolution of the spectrometer and chemical state of the emitting atom. Besides, even in the absence of the Auger signal, the amplitude of the derivative is not zero due to the statistical variation of the signal and electronic noise. Several effects contribute to the result that the derivative of the peak 30 assumes a non-zero value 32. Furthermore, Auger transitions in many chemical elements form a series of overlapping peaks, and the separation of overlapping derivative peaks is cumbersome.

Another method for measuring the intensity of an Auger peak integrates the area under the Auger peak. This method requires that the Auger peaks be separated from the inelastic background. Because each electron inside the solid produces an avalanche of inelastically scattered electrons, the low energy side of Auger peaks gradually merges with the inelastic background. Furthermore, to increase the sensitivity of this method, it is frequently desirable to decrease the resolution of the spectrometer. In industrial applications, such low resolution spectrometers enjoy reduced cost. Under such circumstances, the separation of the Auger peak from the background is rather difficult, especially in the case of low intensity Auger peaks and Auger peaks arising from low-level impurities.

Accordingly, it is desired to provide a more accurate method in Auger spectroscopy and other electron spectroscopy of measuring small compositions of impurities. It is particularly desired to measure small compositions of impurities in carbon films.

SUMMARY OF THE INVENTION

A method and apparatus for extracting peak intensities in an electron analyzer, especially useful for determining compositions by means of Auger spectroscopy. An electron spectrum is measured on either side of the anticipated peak position, for example, an Auger peak of one of the known constituents of the sample being measured. The data on either side of the peak are fit to respective function relationships, typically linear equations depending upon the electron energy. However, the data close to the peak and experiencing significant variations with energy are not fit. The difference in the two functional relationships near the anticipated peak is associated with the peak intensity and hence the composition of the element producing the peak.

The invention is particularly useful in determining concentrations of a known impurity in thin films of simple composition, for example, nitrogen in carbon film.

DETAILED DESCRIPTION OF THE PREFERRED EMBODIMENTS

One aspect of the invention allows the analysis of Auger data to more simply and accurately determine impurity concentrations, particularly in the case when there are very few elements and associated peaks, because the peak positions are already well known.

Figure 4:
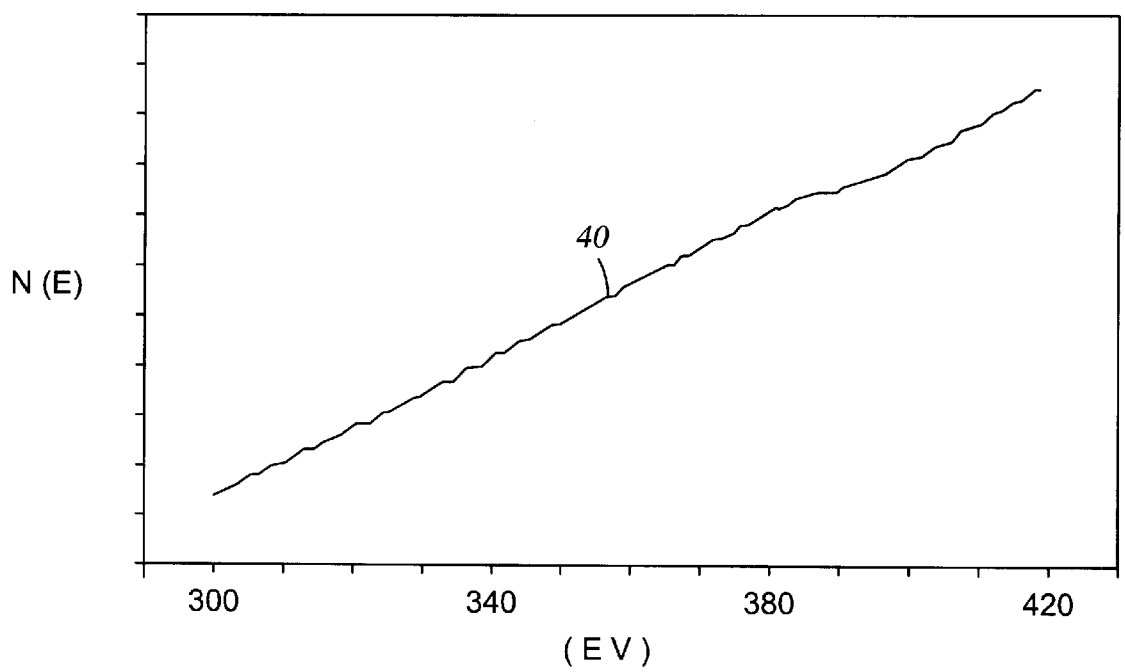
FIG. 4 is an intensity spectrum for electron measured in a system with degraded resolution.
Figure 5:
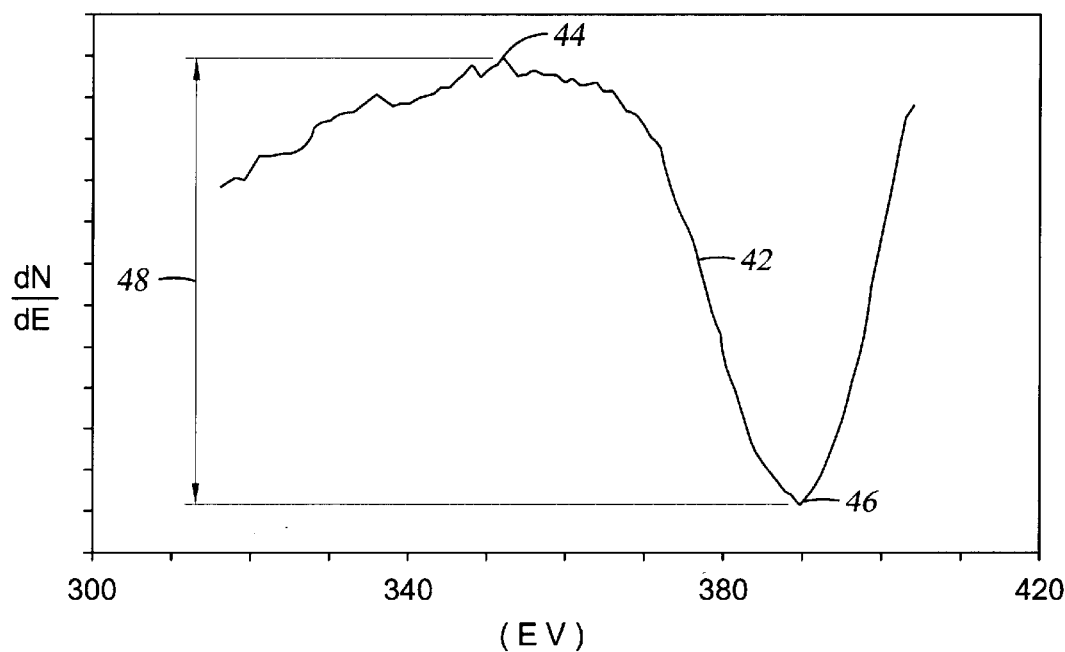
FIG. 5 is a intensity derivative spectrum taken from the intensity data of FIG. 4.

The graph of FIG. 4 shows a spectrum 40 experimental intensity data N(E) as a function of energy E of the detected secondary electrons when the primary electron energy is about 5 keV. The intensity scale is linear but is offset from zero by an arbitrary amount. A nitrogen Auger peak associated with the KVV transition is anticipated at around 392 eV The conventional analysis of this data produces a derivative spectrum 42 shown in FIG. 5. The peak position is somewhere between subsidiary peaks 44, 46 at 350 and 390 eV. The peak intensity is identified with a difference 48 in the derivative values at the subsidiary peaks 44, 46. However, this determination is considered very suspect because it is taken over an energy difference of more than 10% of the energy of interest, and the background level may well be varying other than linearly in this range.

Figure 6:
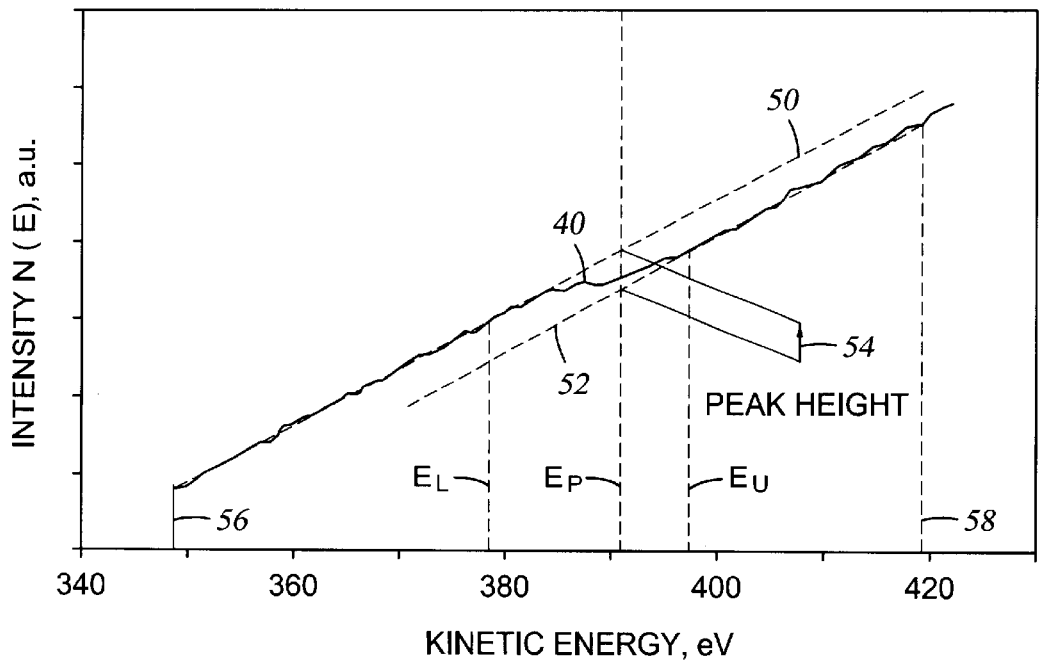
FIG. 6 is an explanatory graph using an expanded portion of the intensity spectrum of FIG. 4 and illustrating the two curves to which the data are fit according to the invention.

According to the invention, the intensity data of the spectrum 40 of FIG. 4 is instead directly analyzed, as will be explained with reference to FIG. 6 showing a reduced range of the same data 40 with vertical expansion. For the anticipated peak, here at about a peak energy $E_P$ of 392 eV, a lower energy limit $E_L$ and an upper energy limit $E_U$ are determined which separate the peak area from the surrounding gently varying background. The data for energies less than the lower limit $E_L$ are fit through data analysis such as least square analysis to a first linear equation $$N(E \leq E_L) = A + \alpha E \quad (1)$$

shown as line in 50 in FIG. 6. Similarly, the data for energies greater than the upper limit $E_U$ is fit to a second linear equation $$N(E \geq E_U) = B + \beta E \quad (2)$$

shown as line 52. The two fits produce the four fitting parameters A, B, $\alpha$, and $\beta$. The concentration $C_P$ associated with the element of the Auger peak is identified with the difference 5434 between these two linear fits at the peak energy $E_P$, that is, $$C_P = c[A - B + (\alpha - \beta) E_P]. \quad (3)$$

The value of the proportionality constant c, which converts measured intensity to concentration, depends on the experimental setup but should remain the same between measurements of different samples. Therefore, once the measurement has been normalized to a sample of known composition or to a sample established as a baseline, subsequent measurements will determine at least a proportional change of composition relative to the calibration sample.

The derivation of Equation (3) implicitly assumes that the impurity concentration is relatively low. The measurement range can be expanded to a wider range of concentrations by comparing the intensities of the peaks of the major components. For example, in the situation of a two-component system, the concentration of the one component is given by $$C_1 = \frac{\alpha_1 I_1}{\alpha_1 I_1 + \alpha_2 I_2}, \qquad (4)$$

where $I_1$ and $I_2$ are the peak intensities of the two components separately measured by the method of, for example, Equations (1) to (3), and $\alpha_1$ and $\alpha_2$ are the elemental Auger sensitivities of the two components, which are well known parameters. This equation can be extended to more components in an obvious way as long as the peaks do not overlap.

In most circumstances, the limits $E_L$ and $E_U$ should be placed as close as practical to the anticipated peak energy $E_P$ as long as they remain on the linear parts of the spectrum. The illustrated values of 378 eV and 397 eV for the 392 eV nitrogen peak are illustrative. The measurement system may be used in a production environment to monitor the production output, for example, to monitor the nitrogen content of a protective amorphous carbon film. In these situations, the limits $E_L$ and $E_U$ may be set by trial and error to arrive at values residing in the linear parts of the spectrum for different impurity concentrations and which in turn allow the data analysis to produce reliable impurity concentrations. Outer limits 56, 58 of the data to be analyzed, for example, the 348 eV and 419 eV of FIG. 6, extend far enough from the range of the peak energy $E_P$ to allow the generation of data over significant energy range in a reasonable length of time. A further 10% to 20% beyond the limits $E_L$ and $E_U$ produces good results. However, care must be taken to avoid any other peaks and their tails, which would severely impact the linearity of the data. As should be apparent from an inspection of the data of FIG. 6, since the two curves 50, 52 have nearly the same slope, the exact identification of the peak energy $E_P$ is not crucial, and little inaccuracy arises if the difference of the two curves 50, 52 is measured at another energy between the two limits $E_L$, $E_U$.

Although the form fitting was performed with two linear equations, it is appreciated that more complex equations may be used to fit the data. However, it has been found that the linear equations are quite adequate. It is also appreciated that the data analysis represented by Equations (1) to (3) may be performed in other ways not requiring the explicit calculations of the four parameters of the two linear equations. It is also appreciated that the spectra need not be referenced to the electron energy itself, but other operational parameters associated with the electron energy, such as retarding voltage or magnetic deflection field, may be used as the functional parameter as long as the associated value of the anticipated peak is known in these terms.

The process thus includes the selection of the limits $E_L$ and $E_U$ on either side of a range including the anticipated peak energy $E_P$ for a given element, obtaining electron intensity data for a set of lower energies below the lower limit $E_L$ and for a set of upper energies above the upper limit $E_U$, fitting the lower energies to a first relationship such as a first equation linearly dependent on energy, fitting the upper energy to a second relationship such as a second equation linearly dependent on energy, and equating a difference in energy between the two relationships within the range between $E_L$ and $E_U$ to the concentration of the element.

Figure 1:
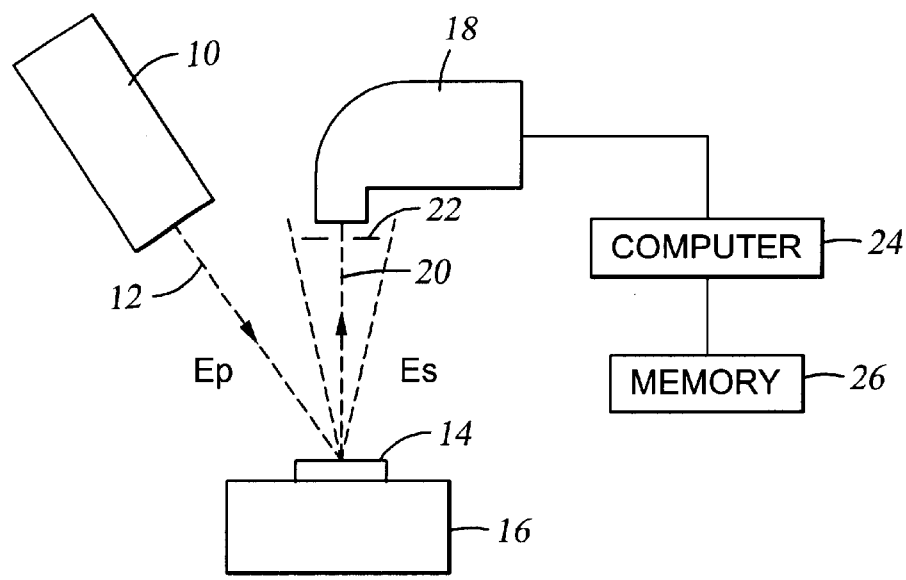
FIG. 1 is a schematic representation of an electron analyzer system, such as an Auger spectrometer.
Figure 2:
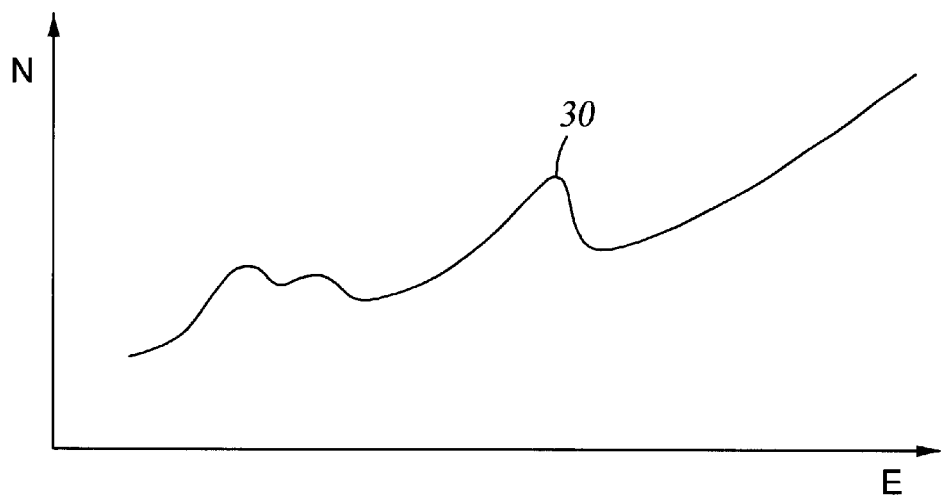
FIG. 2 is a typical intensity spectrum for an Auger energy analysis of the prior art.
Figure 3:
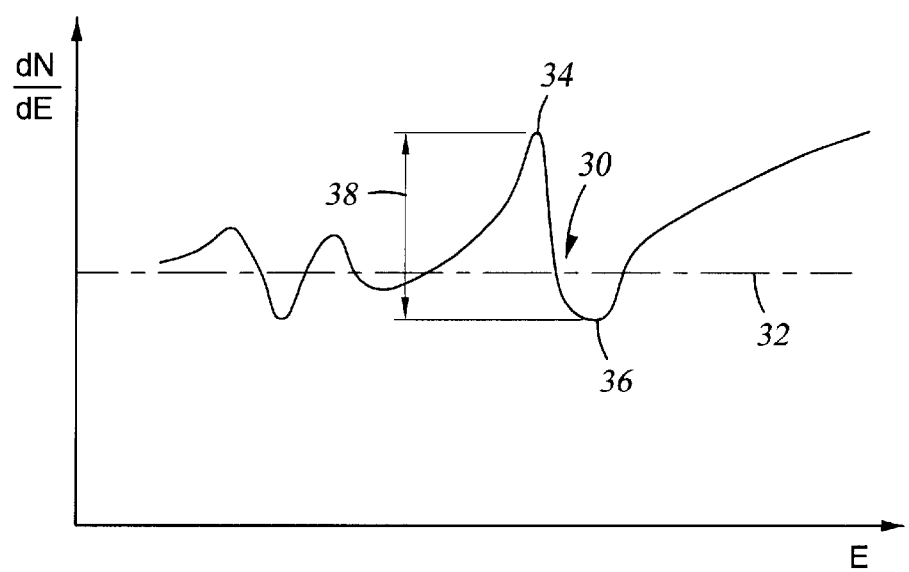
FIG. 3 is a intensity derivative spectrum taken from the data of FIG. 2 and typically used in the past to measure a peak intensity.

It is anticipated that the analysis process of the invention will be implemented in software means programmed into the computer 24 of FIG. 1 relying upon a complete intensity spectrum recorded into the memory 26. However, as needed, the analysis may be off loaded to another computer or performed by hard-wired logic.

Although the invention has been described with reference to Auger spectroscopy it is not necessarily so limited and may be applied to other electron spectroscopy exhibiting small peaks in a large rising background.

The invention provides several advantages over the conventional derivative method.

The derivative method shows a generally positive amplitude even in the absence of an Auger peak because of the statistical nature of the background intensity. The invention is almost as likely to produce positive and negative intensities in the absence of a true Auger signal.

Because of inelastic scattering, the Auger spectra are asymmetric about the peak energy. The intensity of the low energy tail of the peak changes much more slowly than the high energy tail. As a result, small variations of the low energy background can lead to a large displacements of the maximum of the intensity derivative. Further, in some cases, the derivative gradual rises with decreasing kinetic energy. In these cases, the standard algorithm produces different intensities depending on the width of the window in which the spectrum was measured. The step function of the invention is much more reliable with respect to the shape of the background.

The amplitude of the derivative signal depends strongly on the system resolution. The step function is much less dependent on the system resolution. As a result, the invention allows the accurate determination of relatively low concentrations of impurities in production samples. Nonetheless, this capability is achievable with only minor changes to the software used to analyze data which are already available in prior art analyzers.

What is claimed is:

1. A method of analyzing data obtained from an electron energy analyzer in which a beam of probing electrons irradiates a sample and the electron energy analyzer measures intensities of resultant electrons emitted from said sample, said method comprising the steps of:

measuring a first set of electron intensities for a plurality of electron energies in a first range of measurement energies less than a given energy by at least a first predetermined energy;

measuring a second set of electron intensities for a plurality of electron energies in a second range of measurement energies greater than said given energy by at least a first predetermined energy;

fitting a first expression to said first set of electron intensities;

fitting a second expression to said second set of electron intensities; and determining a difference between said first and second expressions at said given energy.

2. The method of claim 1, wherein said given energy corresponds to an Auger energy of an element and wherein said difference is identified with a concentration of said element in said sample.

3. The method of claim 2, wherein said element is nitrogen.

4. The method of claim 3, wherein surface region of said sample probed by said probing electrons principally composes carbon.

5. The method of claim 1, wherein said first and second expressions are respective equations linearly dependent upon said measurement energies.

6. A method of analyzing an electron intensity spectrum, comprising the steps of:

measuring electron intensities of electrons emanating from a sample as a function of values of a measurement parameter associated with measurement energies on either side of an anticipated peak energy in said spectrum;

fitting a first portion of said spectrum above said anticipated peak energy to a first equation dependent upon said measurement parameter;

fitting a second portion of said spectrum below said anticipated peak energy to a second equation dependent upon said measurement parameter; and associating a comparison between said two equations with a concentration of an element in said sample.

7. The method of claim 6, wherein said comparison is a difference in said two equations at said anticipated peak energy.

8. The method of claim 6, wherein said anticipated peak energy is an energy of an Auger transition of said element in said sample.

9. The method of claim 6, wherein said first and second equations are linearly dependent upon said measurement energy.

10. An electron spectrometer system, comprising:

a source of primary electrons for irradiating a sample;

an electron energy analyzer for measuring an intensity spectrum and measurement parameter of electrons emitted from said sample in response to said primary electrons and storing said spectrum in a memory;

first calculation means for fitting a first portion of said spectrum in a first predetermined range of said measurement parameter less than a given measurement parameter value to a first expression dependent upon said measurement parameter and for fitting a second portion of said spectrum in a second predetermined range of said measurement parameter greater than said given measurement parameter value of to a second expression dependent upon said measurement parameter; and second calculation means for establishing a difference between said first and second expressions at said given measurement parameter value.

11. The analyzer system of claim 10, wherein said measurement parameter is an energy of said electrons emitted from said sample.

12. The analyzer system of claim 10, wherein said first and second expressions are equations linearly dependent upon said measurement parameter.

13. The analyzer system of claim 10, wherein said given measurement parameter value corresponds to an Auger transitions of a constituent of said sample.

14. The analyzer system of claim 13, wherein said difference is associated with a concentration of said constituent in said sample.

* * * * *